United States Patent [19]

Nishimura et al.

[11] 3,957,788
[45] May 18, 1976

[54] 1-SUBSTITUTED-4-(1,2-DIPHENYLETHYL)-PIPERAZINE DERIVATIVES AND THEIR SALTS AND THE PREPARATION THEREOF

[75] Inventors: Haruki Nishimura, Ikeda; Hitoshi Uno, Takatsuki; Kagayaki Natsuka, Ibaraki; Noriaki Shimokawa, Nagaokakyo; Masanao Shimizu, Kobe; Hideo Nakamura, Tenri, all of Japan

[73] Assignee: Dainippon Pharmaceutical Co., Ltd., Osaka, Japan

[22] Filed: Jan. 15, 1975

[21] Appl. No.: 541,351

[30] Foreign Application Priority Data

Jan. 23, 1974 Japan.................................. 49-10470
Mar. 12, 1974 Japan.................................. 49-28296
Mar. 14, 1974 Japan.................................. 49-29683

[52] U.S. Cl...................... 260/268 PH; 260/268 R; 424/250
[51] Int. Cl.². ...................................... C07D 295/08
[58] Field of Search................. 260/268 PH, 268 R; 424/250

[56] References Cited
OTHER PUBLICATIONS

Umemoto; Susumi et al., C. A. Vol. 77, p. 5521v, (1972).

*Primary Examiner*—Raymond V. Rush
*Assistant Examiner*—Jose Tovar
*Attorney, Agent, or Firm*—Stevens, Davis, Miller & Mosher

[57] ABSTRACT

1-Substituted-4-(1,2-diphenylethyl)piperazine derivatives of the formula:

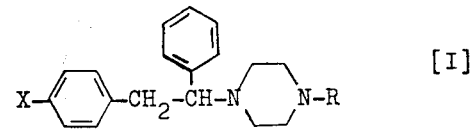

wherein X is hydroxy, methoxy, methyl or trifluoromethyl; and R is an unsubstituted monocycloalkyl group having 6 to 8 carbon atoms or 2-methoxyphenyl; provided that when X is hydroxy, R is cyclohexyl, and when X is trifluoromethyl, R is 2-methoxyphenyl, and their pharmaceutically acceptable salts, which have excellent analgesic, anti-tussive and anti-inflammatory activities, without undesirable side effect such as narcotic activity, and a process for the preparation thereof.

23 Claims, No Drawings

1-SUBSTITUTED-4-(1,2-DIPHENYLETHYL)PIPERAZINE DERIVATIVES AND THEIR SALTS AND THE PREPARATION THEREOF

The present invention relates to novel, pharmaceutically active 1-substituted-4-(1,2-diphenylethyl)piperazine derivatives and their pharmaceutically acceptable salts and the preparation thereof. More particularly, it relates to 1-substituted-4-(1,2-diphenylethyl)piperazine derivatives of the following formula:

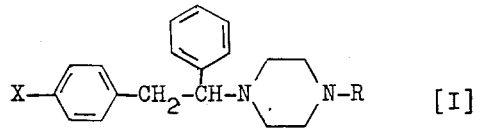 [I]

wherein X is hydroxy, methoxy, methyl or trifluoromethyl; and R is an unsubstituted monocycloalkyl group having 6 to 8 carbon atoms or 2-methoxyphenyl; provided that when X is hydroxy, R is cyclohexyl, and when X is trifluoromethyl, R is 2-methoxyphenyl, and their pharmaceutically acceptable salts, and further the preparation thereof.

Some compounds having an analogous structure to that of the present compounds have been already described in Japanese Patent Publication Nos. 6304/1972 and 188/1974 and The Japanese Journal of Pharmacology, Vol. 22, page 88 (April 27, 1972), etc. These known compounds have been prepared by some of the present inventors and some compounds have a comparatively excellent analgesic activity. However, such compounds have a morphine-like drug dependence liability or too strong toxicity, and therefore, they can hardly be used as a medicine excepting the use for a specific purpose.

The present inventors have extensively studied to find a novel compound having excellent analgesic activity without such undesirable side effect, and then found that the novel piperazine derivatives of the formula [I] and their pharmaceutically acceptable salts exhibit superior pharmacological activities, such as analgesic, anti-tussive and anti-inflammatory activities and are less toxicity and free from narcotic activity, and therefore, they are useful as a medicine.

An object of the present invention is to provide novel piperazine derivatives and their pharmaceutically acceptable salts having excellent pharmacological activities without undesirable side effects.

Another object of the invention is to provide a process for the preparation of the piperazine derivatives and their pharmaceutically acceptable salts.

A further object of the invention is to provide a pharmaceutical composition containing the compound as set forth above as the active ingredient.

Still further object of the invention is to provide the use of the compound as set forth above as an analgesic.

These and other objects will be apparent from the description hereinafter.

The compounds of the present invention include those represented by the formula [I] as shown hereinbefore and their pharmaceutically acceptable salts. Suitable compounds of the present invention are as follows:

1-Cyclohexyl-4-[2-(4-methoxyphenyl)-1-phenylethyl]-piperazine and its pharmaceutically acceptable acid addition salt 1-Cycloheptyl-4-[2-(4-methoxyphenyl)-1-phenylethyl]-piperazine and its pharmaceutically acceptable acid addition salt 1-(2-Methoxyphenyl)-4-[1-phenyl-2-(4-tolyl)ethyl]-piperazine and its pharmaceutically acceptable acid addition salt The present compounds have an asymmetric carbon in the molecule, and therefore, optical isomers exist. The present invention includes all these racemic or optically resolved products. Preferred one is the racemic product.

The compounds of the present invention have the advantages as summarized as follows:
1. They show superior analgesic activity.
2. They are non-narcotic, i.e. they do not show any morphine-like drug dependence liability.
3. They show low toxicity.
4. They show superior activities by oral administration.
5. Some compounds show also excellent anti-tussive and anti-inflammatory activities.
6. They are useful in a racemic form, and therefore, no resolution is required for obtaining active substance, which is economical.

The excellent activities of the present compounds are demonstrated by the following experimental tests.

1. Drum dependence liability:
   i. Mouse jumping test (Cf. J. K. Saelens, F. R. Granat and W. K Sawyer, Arch. int. Pharmacodyn., Vol. 190, page 213, 1971; and J. Nakamura, Y. Yokoyama, S. Motoyoshi and M. Shimizu, Folia Pharmacologica Japonica, Vol. 69, page 326p, 1973)

Male mice of ddN strain, weighing 19 to 23 g, were used. The test compounds were subcutaneously and/or orally given in increasing increments of 8, 16, 25, 50 and 100 mg/kg or until a maximally tolerated dose was reached within that range. Two hours after the last injection, the animals received intraperitoneal injections of 50 mg/kg of nalorphine hydrochloride. The number of jumps and the height of jumps made by each mouse during the 30 minutes period after the injection of the morphine antagonist were recorded.

ii. Straub tail index (Cf. Irving Shemano and Herbert Wendel, Toxicology and Applied Pharmacology, Vol. 6, page 334, 1964)

Graded doses of compounds were rapidly injected intravenously through the tail vain of male mice of ddN strain, weighing 18 to 22 g, in a volume of 0.1 ml per 10 g body weight. The criterion for Straub tail was erection of the tail to 90 degrees or greater within 20 minutes after the injection of the test compounds. The Straub tail $ED_{50}$-value and intravenous $LD_{50}$-value for each compound were determined, and the Straub index, the ratio of $LD_{50}$ to Straub tail $ED_{50}$, was calculated.

iii. Substitution test in morphine-dependent rats (Cf. O. J. Lorenzetti and L. F. Sancilio, Arch. int. Pharmacodyn., Vol. 183, page 391, 1970; and S. Nurimoto, Japan. J. Pharmacol., Vol. 23, page 401, 1973)

Male rats of Wistar strain, weighing 200 to 250 g, received morphine hydrochloride subcutaneously twice daily. The initial dose of 20 mg/kg was increased weekly by 20 mg/kg until a maintenance of 100 mg/kg × 2/day was attained. The animals received two subcutaneous or oral administrations of a test compound instead of morphine hydrochloride. The withdrawal symptoms were determined and the percent reduction of each withdrawal symptom was calculated from the scores of test compound and vehicle control groups.

These test results are shown in the following Table 1.

Table 1

| Test compound* | Jumping test | Straub tail index | Substitution test |
|---|---|---|---|
| A | (−) | (−) | (−) |
| B | (−) | (−) | (−) |
| C | (−) | (−) | (−) |
| D | (−) | (−) | (−) |
| E | (−) | (−) | |
| F | (−) | (−) | |
| G | (−) | (−) | (−) |
| H | (−) | (−) | (−) |
| I | (−) | (−) | |
| J | (−) | (−) | |
| Reference compound | | | |
| 1 | (+) | (+) 7.34 | (+) |
| 2 | (+) | (+) 30 | (+) |
| 3 | (+) | (+) ca.44 | (+) |
| 4 | (+) | (+) 33.1 | (+) |
| 5 | (−) | (−) | (−) |

Note:
*The test compounds are as follows:
A: dl-1-Cyclohexyl-4-[2-(4-methoxyphenyl)-1-phenylethyl]piperazine.2HCl
B: dl-1-Cyclohexyl-4-[2-(4-hydroxyphenyl)-1-phenylethyl]piperazine.2HBr
C: dl-1-Cyclohexyl-4-[1-phenyl-2-(4-tolyl)-ethyl]piperazine.2HCl
D: dl-1-Cycloheptyl-4-[2-(4-methoxyphenyl)-1-phenylethyl]piperazine.2HCl
E: dl-1-(2-Methoxyphenyl)-4-[2-(4-methoxyphenyl)-1-phenylethyl]piperazine.2HCl
F: dl-1-Cyclooctyl-4-[2-(4-methoxyphenyl)-1-phenylethyl]piperazine.2HCl
G: dl-1-Cycloheptyl-4-[1-phenyl-2-(4-tolyl)ethyl]-piperazine.2HCl
H: dl-1-(2-Methoxyphenyl)-4-[1-phenyl-2-(4-tolyl)-ethyl]piperazine.2HCl
I: dl-1-(2-Methoxyphenyl)-4-[1-phenyl-2-(4-trifluoromethylphenyl)ethyl]-piperazine.2HCl
J: dl-1-Cyclooctyl-4-[1-phenyl-2-(4-tolyl)ethyl]-piperazine.2HCl
1: dl-1-Cyclohexyl-4-(1,2-diphenylethyl)piperazine.2HCl (disclosed in Japanese Patent Publication No. 6304/1972)
2: d-1-Cyclohexyl-4-(1,2-diphenylethyl)piperazine.2HCl (disclosed in Japanese Patent Publication No. 188/1974)
3: dl-4-(1,2-Diphenylethyl)-1-(2-methoxyphenyl)piperazine.2HCl (disclosed in Japanese Patent Publication No. 6304/1972)
4: Morphine hydrochloride
5: Aminopyrine (commercially available analgesic)

2. Analgesic activity:

i. D'Amour-Smith method (Cf. F. E. D'Amour and D. L. Smith, J. Pharmacol., Vol. 72, page 74, 1941)

Thermal pain was induced by radiating heat light on the tail blacked with a black ink of male mice of ddN strain, weighing 9 to 12 g, using the modified apparatus of D'Amour-Smith. The analgesic $ED_{50}$-value was calculated from the number of positive animals showing the response time prolonged more than 100 % compared with each before value.

ii. Haffner method (Cf. F. Haffner, Deut. Med. Wochschr., Vol. 55, page 731, 1929)

Mechanical pain was induced by pressing the tail of male rats of Wistar strain, weighing 90 to 110 g, using the modified apparatus of Haffner. The analgesic $ED_{50}$-value was calculated from the number of positive animals showing pain threshold of 40 mm or more (normal value is about 20 mm).

iii. Phenylquinone method (Cf. E. Siegmund, R. Cadmus and G. Lu, Proc. Soc. Exptl. Biol. Med., Vol. 95, page 792, 1957)

Chemical pain was induced by an intraperitoneal injection of 0.1 ml/10 g body weight of 0.03 % phenylquinone in 5 % aqueous ethanol in female mice, weighing 18 to 22 g of ddN strain. Drugs were given 30 minutes before challenge of phenylquinone.

The test results are shown in the following Table 2.

Table 2

| Test compound* | D'Amour-Smith method | | Phenylquinone method | Haffner method |
|---|---|---|---|---|
| | p.o. | s.c. | p.o. | p.o. |
| A | 164 | 74.2 | 39.0 | 180 |
| B | 84 | 13.1 | 58.3 | 96.3 |
| D | 137.9 | — | 25.8 | 94.5 |
| E | 256 | — | 38.5 | 29.3 |
| F | 48.1 | — | 27 | — |
| H | 283 | — | 49.4 | — |
| I | ca.200 | — | — | — |
| J | 177 | — | 48 | — |
| Reference compound | | | | |
| 6 | 116 | 50.7 | 73.3 | 118.0 |
| 7 | >1280 | — | 83 | — |
| 8 | >160 | 46.6 | 52.3 | >240 |
| 5 | ≧ 640 | 233 | 53.3 | >2560 |

Note:
*The test compounds A, B, D, E, F, H, I and J and the Reference compound 5 are as defined in Table 1, and other Reference compounds are as follows:
6: 1-1-Cyclohexyl-4-(1,2-diphenylethyl)piperazine.2HCl (disclosed in Japanese Patent Publication No. 188/1974)
7: dl-4-[2-(4-Chlorophenyl)-1-phenylethyl]-1-(2-methoxyphenyl)piperazine.2HCl
8: 1-1,2-Diphenyl-1-dimethylaminoethane.HCl (disclosed in German Patent No. 1,159,958)

3. Toxicity:

i. Acute lethal toxicity

Male mice of ddN strain, weighing 18 to 26 g, and male rats of Wistar strain, weighing 200 to 300 g, were used. The test compounds were dissolved in saline or suspended in 0.5 % gum tragacanth aqueous solution, and administered subcutaneously, intraveneously or orally. The value of $LD_{50}$ was calculated according to Litchfield-Wilcoxon method. The results are shown in the following Table 3.

Table 3

| Test compound* | Mice | | Rats | |
|---|---|---|---|---|
| | p.o. | i.v. | p.o. | s.c. |
| A | 440 | 37.0 | 953 | 363 |
| B | 477 | — | ca. 1000 | — |
| C | ca. 1200 | — | ca. 1200 | — |
| D | 464 | 26.0 | 727 | 697 |
| E | >3200 | — | ca. 900 | — |
| F | 538 | — | ca. 800 | — |
| G | 2987 | — | ca. 1000 | — |
| H | >3200 | — | ca. 2100 | — |
| I | ca. 1600 | — | — | — |
| J | >3200 | — | — | — |
| Reference compound | | | | |
| 6 | 250 | 17.9 | 288 | 97.7 |
| 8 | 176 | — | ca. 300 | — |
| 9 | 246 | — | ≦ 160 | — |

Note:
*The test compounds A to J and the Reference compounds 6 and 8 are as defined in Table 1 and Table 2, and other Reference compound 9 is as follows:
9: dl-4-[2-(4-Chlorophenyl)-1-phenylethyl]-1-cyclohexylpiperazine.2HCl ii. Subacute toxicity Male rats of Wistar strain, weighing 140 to 160 g, were used. The test compound A was orally administered once a day for 4 weeks in a dose of 100 mg/kg/day. No abnormal symptom was observed in the test animals.

4. Anti-tussive activity (Cf. K. Takagi, H. Fukuda and K. Yano, Yakugakuzasshi, Vol. 80, page 1497, 1960)

Male guinea pigs, weighing 500 to 600 g, were used. Coughs were caused by successive mechanical stimulations with whiskers, and anti-tussive effects were evaluated by all or none of the cough. The test compounds A and G were intraperitoneally injected. As the results, the test compounds showed excellent anti-tussive activity in a dose of 160 mg/kg (about 1/4 of codeine phosphate).

5. Anti-inflammatory activity:

The activity was determined by carrageenin-induced hind paw oedema (Cf. C. A. Winter, E. A. Risley and G. G. Nuss, Proc. Soc. Exp. Biol. Med., Vol. 111, page 544, 1962).

Male rats of Wistar strain, weighing 100 to 120 g, were used, Hind paw oedema was induced by subcutaneous injection of 0.1 ml of 1 % carrageenin into the right foot pad of each rat. The value of $ED_{50}$ was calculated according to Litchfield-Wilcoxon method using the number of positive rats, which showed the inhibitory effect of 25 % or more than the corresponding vehicle control group at 3 hours after the challenge of carrageenin. The test compounds A and B were orally administered one hour before challenge of carrageenin. As the results, the test compounds showed excellent anti-inflammatory activity similar to that of aminopyrine.

The compounds [I] and their pharmaceutically acceptable salts of the present invention may be used as medicines, for example, in the form of pharmaceutical preparations containing the compound in admixture with an organic or inorganic, solid or liquid pharmaceutical adjuvants suitable for oral or parenteral administration. Pharmaceutically acceptable adjuvants are substances that do not react with the compounds, for example, water, gelatin, lactose, starch, cellulose, preferably microcrystalline cellulose, sodium carboxymethyl cellulose, calcium carboxymethyl cellulose, methyl cellulose, sorbitol, magnesium stearate, talc, vegetable oils, benzyl alcohol, gums, propylene glycol, polyalkylene glycols, methylparaben and other known medicinal adjuvants. The pharmaceutical preparations may be, for example, powder, tablets, suppositories, or capsules, or in liquid form as solutions, suspensions, or emulsions. They may further contain other therapeutically valuable substances. The preparations are prepared by conventional methods.

A clinical dosage of the compound [I] or its pharmaceutically acceptable salt depends on body weight, age and administration routes, but it is generally in the range of 10 to 500 mg/day, preferably of 50 to 200 mg/day.

The compounds of the formula [I] and their pharmaceutically acceptable salts of the present invention can be prepared by the following processes (1) to (4).

Process (1):

They may be prepared by reacting a compound of the following formula:

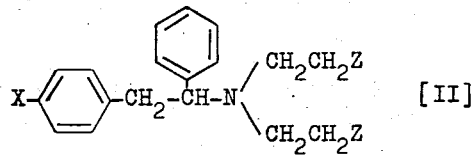

wherein Z is a residue of reactive ester of alcohol, such as halogen (e.g. chlorine or bromine), arylsulfonyloxy (e.g. p-toluenesulfonyloxy or benzenesulfonyloxy) or alkanesulfonyloxy (e.g. methanesulfonyloxy), X is as defined above, or its salts with a compound of the formula:

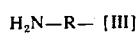

wherein R is as defined above.

The reaction of the Process (1) may be carried out by heating a mixture of the compound [II] with an equimolar or excess amount of the compound [III] in the presence or absence of a solvent, such as an aliphatic alcohol (e.g. aqueous or anhydrous ethanol or isopropanol), an aromatic hydrocarbon (e.g. toluene or xylene), a ketone (e.g. methyl ethyl ketone), an ether (e.g. dioxane), a halogenated hydrocarbon (e.g. ethylene dichloride), dimethylformamide, or dimethyl sulfoxide. Suitable reaction temperature may be 60° to 170°C, and the reaction may usually be carried out at a reflux temperature.

The reaction may be also carried out in the presence of a basic material, such as an alkali metal hydrogen carbonate (e.g. sodium hydrogen carbonate or potassium hydrogen carbonate), an alkali metal carbonate (e.g. sodium carbonate or potassium carbonate), or an organic base (e.g. triethylamine). The reactant of the formula [III] may also be utilized as the basic material by using in an excess amount.

The starting material [II] in the above Process (1) may be prepared, for example, by the following process.

3-(2-Hydroxyethyl)-2-phenyloxazolidine is reacted with a compound of the formula:

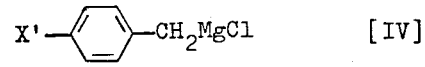

wherein X' is methoxy, methyl or trifluoromethyl, in an inert solvent to give a compound of the formula:

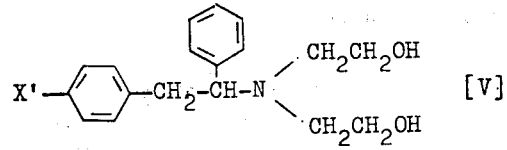

wherein X' is as defined above, or its salt. Subsequently, the compound [V] or its salt thus obtained is reacted with a conventional halogenating agent, such as thionyl chloride, or with a conventional sulfonating agent, such as p-toluenesulfonyl chloride, benzenesulfonyl chloride or methanesulfonyl chloride, to give the desired compound [II] wherein X is X', i.e. methoxy, methyl or trifluoromethyl. When the compound [II] thus obtained (X is methoxy) is subjected to cleavage of the ether linkage by treating it with a cleavage agent for splitting ether, the desired compound [II] wherein X is hydroxy can be obtained. Examples of the cleavage agent for splitting ethers include Lewis acids (e.g. aluminum chloride, aluminum bromide or boron tribromide) and hydrohalogenic acid (e.g. hydrobromic acid, hydroiodic acid or hydrochloric acid).

Process (2):

The compounds [I] and their pharmaceutically acceptable salts may be prepared by reacting a compound of the following formula:

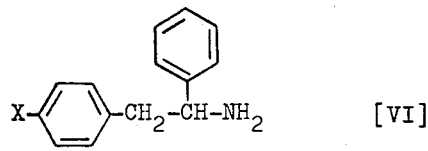

wherein X is as defined above, with a compound of the following formula:

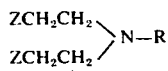 [VII]

wherein R and Z are as defined above, or its salt.

The reaction of the Process (2) may be carried out by heating a mixture of the compound [VII] with an equimolar or excess amount of the compound [VI] in the presence or absence of a solvent in the similar manner as described in Process (1).

The starting material [VI] in the above Process (2) can be prepared in the similar manner as described in Archiv der Pharmazie, Vol. 274, page 153, 1936. Besides, the other starting material [VII] can be prepared in the similar manner as described in Journal of American Chemical Society, Vol. 73, page 3635, 1951, for instance, by reacting N-cyclohexyldiethanolamine with a halogenating or sulfonating agent as described in the Process (1).

Process (3):

The compounds [I] wherein X is methoxy, methyl or trifluoromethyl and their pharmaceutically acceptable salts may be prepared by reacting a compound of the following formula:

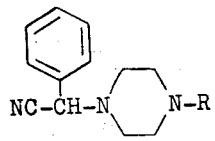 [VIII]

wherein R is as defined above, with a compound of the following formula:

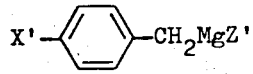 [IX]

wherein Z' is a halogen atom and X' is as defined above.

The reaction of the above Process (3) may be carried out by heating a mixture of the compound [VIII] and an excess amount of the compound [IX] in an inert solvent, such as ether, tetrahydrofuran, n-butyl ether, benzene, or a mixture thereof. Suitable reaction temperature may be from room temperature to 130°C, and the reaction may usually be carried out at a reflux temperature.

The starting material [VIII] in the above Process (3) may be prepared, for example, by reacting under heating a salt of the compound of the following formula:

 [X]

wherein R is as defined above,
with benzaldehyde and sodium cyanide or potassium cyanide in water or an aqueous solvent.

Process (4):

The compound [I] wherein X is hydroxy, i.e. the compound of the following formula:

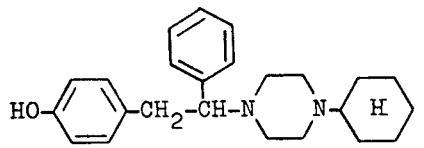 [I']

and its pharmaceutically acceptable salt may be prepared by subjecting a compound of the following formula:

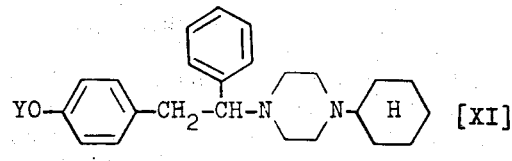 [XI]

wherein Y is an alkyl group having 1 to 7 carbon atoms or benzyl, or its salt to cleavage of the ether linkage by treating it with a cleavage agent for splitting ethers at an elevated temperature in the presence or absence of a solvent, such as water, acetic acid, toluene, xylene, nitrobenzene or chlorobenzene. The reaction may usually be carried out at a reflux temperature.

The cleavage agents for splitting ethers include Lewis acids (e.g. aluminum chloride, aluminum bromide or boron tribromide) and hydrohalogenic acid (e.g. hydrobromic acid, hydroiodic acid or hydrochloric acid).

Basides, when Y in the compound [XI] is benzyl, the cleavage of the ether linkage may be carried out by catalytically reducing it, i.e. by contacting it with an equimolar or slightly excess amount of hydrogen in an inert solvent, such as aqueous or anhydrous methanol, ethanol, water, acetic acid or dioxane, in the presence of a catalyst, such as palladium-carbon, platinum black or Raney nickel, at room temperature or an elevated temperature.

The starting material [XI] in the above Process (4) may be prepared in the similar manner as described in the above Process (2).

In the above processes of the preparation of the present invention, the starting materials and the intermediates may be either in the racemic form or in the optically resolved form when they have an asymmetric carbon in the molecule.

According to the above processes, the desired compounds [I] may be obtained in a form of free base or salt or hydrate depending on the kinds of the starting materials and the reaction conditions. When they are obtained in a form of free base, they may be converted into their pharmaceutically acceptable salts of various inorganic or organic acid. Suitable acids include inorganic acids (e.g. hydrochloric acid, hydrobromic acid, hydroiodic acid, sulfuric acid or phosphoric acid) and organic acids (e.g. citric acid, maleic acid, fumaric acid, tartaric acid, acetic acid, benzoic acid, lactic acid, methanesulfonic acid, 2-naphthalenesulfonic acid, salicyclic acid or acetylsalicyclic acid).

The preparation of the present compounds [I] and their pharmaceutically acceptable salts and further the compositions thereof are illustrated by the following Examples but not limited thereto. In the Examples, percentages are by weight unless otherwise specified.

EXAMPLE 1

Preparation of dl-1-cyclohexyl-4-[2-(4-methoxyphenyl)-1-phenylethyl]piperazine

1. In dimethylformamide (50 ml) is dissolved N,N-bis(2-chloroethyl)-2-(4-metthoxyphenyl)-1-phenylethylamine hydrochloride (18.5 g) and thereto is added cyclohexylamine (19.5 g). The mixture is heated under reflux for 6 hours under stirring. After distilling off the solvent and the excess cyclohexylamine, the residue is dissolved in 10 % hydrochloric acid and the mixture is allowed to cool. The precipitated crystals are collected by filtration and washed with a small amount of cooled water and then with acetone and dried. The product is recrystallized from methanol to give the desired compound as dihydrochloride (16 g), colorless needles, m.p. 243° – 245°C (decomp).

Analysis for $C_{25}H_{34}N_2O \cdot 2HCl$:
Calcd (%): C,66.51; H,8.04; N,6.21; Cl,15.71; Found (%): C,66.28; H,8.30; N,6.14; Cl,15.98.

The free base of the compound is prepared by treating the dihydrochloride obtained above with diluted aqueous potassium carbonate solution by a conventional method, m.p. 96° – 97°C (recrystallized from n-hexane).

Analysis for $C_{25}H_{34}N_2O$: Calcd (%): C,79.32; H,9.05; N,7.40 Found (%): C,79.45; H,8.95; N,7.38.

The maleate of the compound is prepared by treating the compound obtained above with equimolar maleic acid in ethanol by conventional method, m.p. 172° – 175°C (recrystallized from ethanol).

Analysis for $C_{25}H_{34}N_2O \cdot C_4H_4O_4 \cdot 3/2H_2O$: Calcd (%): C,66.78; H,7.92; N,5.37; Found (%): C,66.52; H,7.69; N,5.02

The salicylate of the compound has a melting point of 124° – 126°C (recrystallized from ethanol-n-hexane).

Analysis for $C_{25}H_{34}N_2O \cdot 2C_7H_6O_3$: Calcd (%): C,71.54; H,7.08; N,4.28; Found (%): C,71.74; H,7.06; N,4.58.

2. In dimethylformamide (50 ml) are dissolved N,N-bis(2-chloroethyl)-2-(4-methoxyphenyl)-1-phenylethylamine hydrochloride (17.7 g) and cyclohexylamine (7.9 g) and thereto is added sodium hydrogen carbonate (15 g). The mixture is heated under reflux for 6 hours under stirring. After cooling, the inorganic materials are filtered off and the filtrate is distilled to remove the solvent. The resulting residue is treated in the similar manner as described in (1) to give the desired compound as dihydrochloride (11.4 g), m.p. 243° – 245°C (decomp).

EXAMPLE 2

Preparation of dl-1-cycloheptyl-4-[2-(4-methoxyphenyl)-1-phenylethyl]piperazine

To a solution of N,N-bis(2-chloroethyl)-2-(4-methoxyphenyl)-1-phenylethylamine hydrochloride (19.3 g) in chloroform is added cycloheptylamine (21 g). After chloroform is distilled off, the resulting mixture is heated at 135° – 140°C for 4 hours. The excess cycloheptylamine is distilled off under a reduced pressure, and the residue is dissolved in 10 % hydrochloric acid and the mixture is allowed to cool. The precipitated crystals are collected by filtration and washed with acetone and then recrystallized from methanol to give the desired compound as dihydrochloride (15.5 g), m.p. 241° – 244°C.

Analysis for $C_{26}H_{36}N_2O \cdot 2HCl$: Calcd (%): C,67.09; H,8.23; N,6.02; Cl,15.23; Found (%): C,66.95; H,8.33; N,6.20; Cl,15.30

The free base of the compound has a melting point of 82° – 83°C (recrystallized from n-hexane).

Analysis for $C_{26}H_{36}N_2O$: Calcd (%): C,79.55; H,9.24; N,7.14; Found (%): C,79.52; H,9.20; N,7.01.

EXAMPLE 3

Preparation of dl-1-cyclohexyl-4-[2-(4-hydroxyphenyl)-1-phenylethyl]piperazine

In ethanol (30 ml) are dissolved N,N-bis(2-chloroethyl)-2-(4-hydroxyphenyl)-1-phenylethylamine hydrochloride (1.9 g) and cyclohexylamine (0.7 g), and thereto is added sodium hydrogen carbonate (1.4 g). The mixture is heated under reflux for 30 hours under stirring. After the reaction, the solvent is distilled off and to the residue is added diluted aqueous potassium carbonate. The mixture is extracted with chloroform, and the chloroform layer is washed with water, dried over anhydrous sodium sulfate and then distilled to remove the solvent. The crystalline residue is recrystallized from benzene-n-hexane to give the desired compound (1.0 g), m.p. 197° – 199°C.

Analysis for $C_{24}H_{32}N_2O$: Calcd (%): C,79.08; H,8.85; N,7.68; Found (%): C,79.40; H,9.02; N,7.71.

The above free base is dissolved in a small amount of methanol and the mixture is acidified with 25 % hydrobromic acid-acetic acid. The precipitated crystals are recrystallized from methanol to give dihydrobromide of the compound, colorless needles, m.p. 267° – 268.5°C.

Analysis for $C_{24}H_{32}N_2O \cdot 2HBr$:
Calcd (%): C,54.76; H,6.51; N,5.32; Br,30.37; Found (%): C,54.66; H,6.66; N,5.25; Br,30.35

The monohydrobromide of the compound (colorless prisms) has a melting point of 272° – 274°C (recrystallized from methanol).

Analysis for $C_{24}H_{32}N_2O \cdot HBr$: Calcd (%): C,64.71; H,7.47; N,6.29; Br,17.94; Found (%): C,64.72; H,7.68; N,6.27; Br,17.75.

EXAMPLE 4

Preparation of dl-1-(2-methoxyphenyl)-4-[2-(4-methoxyphenyl)-1-phenylethyl]piperazine In dimethylformamide (50 ml) is dissolved N,N-bis-(2-chloroethyl)-2-(4-methoxyphenyl)-1-phenylethylamine hydrochloride (9.0 g) and thereto is added o-anisidine (11.7 g). The mixture is heated under reflux for 5 hours under stirring. After the reaction, the solvent is distilled off under a reduced pressure, and to the residue is added concentrated aqueous ammonia. The mixture is extracted with ether, and the ether layer is dried over anhydrous potassium carbonate and distilled to remove the solvent. The residual oil is distilled under a reduced pressure to remove the excess o-anisidine. The resulting residue is dissolved in methanol and thereto is added methanolic hydrochloric acid. The crystals thus obtained are recrystallized from methanol to give the desired compound as dihydrochloride monohydrate (6.8 g), m.p. 233° – 236°C.

Analysis for $C_{26}H_{30}N_2O_2 \cdot 2HCl \cdot H_2O$: Calcd (%): C,63.28; H,6.94; N,5.68; Cl,14.37; Found (%): C,63.31; H,6.77; N,5.78; Cl,14.36.

Mass spectrum: m/e 402 ($M^+$)

The free base of the compound has a melting point of 109° – 110°C (recrystallized from ethanol).

Analysis for $C_{26}H_{30}N_2O_2$: Calcd (%): C,77.58; H,7.51; N,6.96; Found (%): C,77.74; H,7.81; N,6.88.

EXAMPLE 5

Preparation of dl-1-(2-methoxyphenyl)-4-[1-phenyl-2-(4-tolyl)ethyl]piperazine

In dimethylformamide (100 ml) is dissolved N,N-bis-(2-chloroethyl)-1-phenyl-2-(4-tolyl)ethylamine hydrochloride (29 g) and thereto is added o-anisidine (38 g).

The mixture is heated under reflux for 5 hours under stirring. The reaction mixture is treated in the similar manner as described in Example 4 and resulting crystals are recrystallized from methanol to give the desired compound as dihydrochloride hemihydrate (22.6 g), m.p. 234° – 238°C.

Analysis for $C_{26}H_{30}N_2O.2HCl.½H_2O$: Calcd (%): C,66.66; H,7.10; N,5.98; Cl,15.14; Found (%): C,66.33; N,7.23; N,5.97; Cl,14.85.

Mass spectrum: m/e 386 (M⁺)

The free base of the compound has a melting point of 129° – 130°C (recrystallized from ethanol).

Analysis for $C_{26}H_{30}N_2O$: Calcd (%): C,80.79; H,7.82; N,7.25; Found (%): C,81.04; H,8.00; N,7.00.

EXAMPLE 6

Preparation of dl-1-(2-methoxyphenyl)-4-[1-phenyl-2-(4-trifluoromethylphenyl)ethyl]piperazine In dimethylformamide (5 ml) is dissolved N,N-bis(2-chloroethyl)-1-phenyl-2-(4-trifluoromethylphenyl)ethylamine hydrochloride (0.8 g) and thereto is added o-anisidine (1.0 g). The mixture is heated under reflux for 5 hours under stirring. The reaction mixture is treated in the similar manner as described in Example 4 and the resulting crystals are recrystallized from methanol to give the desired compound as dihydrochloride (0.5 g), m.p. 222° – 225°C.

Analysis for $C_{26}H_{27}N_2OF_3.2HCl$: Calcd (%): C,60.82; H,5.69; N,5.46; Cl,13.81; Found (%): C,60.75; H,5.98; N,5.75; Cl,13.62.

EXAMPLE 7

The following compounds are prepared in the similar manner as described in Example 1.

dl-1-Cyclohexyl-4-[1-phenyl-2-(4-tolyl)ethyl]piperazine dihydrochloride, m.p. 252° – 256°C Analysis for $C_{25}H_{34}N_2.2HCl$: Calcd (%): C,68.96; H,8.33; N,6.43; Cl,16.28; Found (%): C,68.85; H,8.43; N,6.46; Cl,16.41.

dl-1-Cyclooctyl-4-[2-(4-methoxyphenyl)-1-phenylethyl]-piperazine dihydrochloride, m.p. 241° – 245°C Analysis for $C_{27}H_{38}N_2O.2HCl$: Calcd (%): C,67.63; H,8.41; N,5.84; CL,14.79; Found (%): C,67.45; H,8.36; N,6.09; Cl,15.00.

dl-1-Cycloheptyl-4-[1-phenyl-2-(4-tolyl)ethyl]piperazine dihydrochloride, m.p. 253° – 256°C Analysis for $C_{26}H_{36}N_2.2HCl$:

Calcd (%): C,69.47; H,8.52; N,6.23; Cl,15.77; Found (%): C,69.37; H,8.63; N,6.28; Cl, 15.96.

dl-1-Cyclooctyl-4-[1-phenyl-2-(4-tolyl)ethyl]piperazine dihydrochloride, m.p. 249° – 253°C Analysis for $C_{27}H_{38}N_2.2HCl$:

Calcd (%): C,69.96; H,8.70; N,6.04; Cl,15.30; Found (%): C,69.90; H,8.92; N,5.97; Cl, 15.53

EXAMPLE 8

Preparation of dl-1-cyclohexyl-4-[2-(4-methoxyphenyl)-1-phenylethyl]piperazine

1. In dimethylformamide (30 ml) are dissolved 2-(4-methoxyphenyl)-1-phenylethylamine (6.8 g) and N-cyclohexyl-2,2'-dichlorodiethylamine hydrochloride (2.6 g), and the mixture is heated under reflux for 6 hours under stirring. The solvent is distilled off under a reduced pressure, and the residue is dissolved in 10 % hydrochloric acid and the mixture is allowed to cool. The precipitated crystals are collected by filtration, washed with a small amount of cooled water and then with acetone and dried. The crystals are recrystallized from methanol to give the desired compound as dihydrochloride (2.6 g), colorless needles, m.p. 243°– 245°C (decomp).

2. In dimethylformamide (30 ml) are dissolved 2-(4-methoxyphenyl)-1-phenylethylamine (4.5 g) and N-cyclohexyl-diethanolamine di-p-toluenesulfonate hydrochloride (2.7 g), and the mixture is heated under reflux for 5 hours under stirring. The solvent is distilled off under a reduced pressure, and to the residue is added diluted aqueous sodium carbonate solution to make it alkaline. The mixture is extracted with ether, and the ether layer is washed with water, dried over anhydrous sodium sulfate and then distilled to remove the solvent. The resulting residue is treated with ethanolic hydrochloric acid. The resulting crystals are recrystallized from methanol to give the desired compound as dihydrochloride (0.4 g), m.p. 243° – 245°C (decomp).

EXAMPLE 9

Preparation of dl-1-cycloheptyl-4-[2-(4-methoxyphenyl)-1-phenylethyl]piperazine

To 2-(4-methoxyphenyl)-1-phenylethylamine (6.8 g) is added a solution of N-cycloheptyl-2,2'-dichlorodiethylamine hydrochloride (2.7 g) in chloroform, and then the chloroform is distilled off. The resulting mixture is heated at 135°– 140°C for 4 hours. The reaction mixture is treated in the similar manner as described in Example 8, (1), and the resulting crystals are recrystallized from methanol to give the desired compound as dihydrochloride (2.3 g), m.p. 241° – 244°C.

EXAMPLE 10

Preparation of dl-1-cyclohexyl-4-[2-(4-hydroxyphenyl)-1-phenylethyl]piperazine

In ethanol (60 ml) are dissolved 2-(4-hydroxyphenyl)-1-phenylethylamine (3.0 g) and N-cyclohexyl-2,2'-dichlorodiethylamine hydrochloride (2.6 g), and thereto is added sodium hydrogen carbonate (2.8 g). The mixture is heated under reflux for 20 hours under stirring. The solvent is distilled off under a reduced pressure, and to the residue is added 10 % hydrochloric acid (20 ml) and the mixture is allowed to cool. The resulting crystals are recrystallized from methanol to give the desired compound as dihydrochloride (2.5 g), m.p. 263° – 265°C.

Analysis for $C_{24}H_{32}N_2O.2HCl$: Calcd (%): C,65.90; H,7.83; N,6.40; Cl,16.21; Found (%): C,65.86; H,7.63; N,6.28; Cl,15.99.

EXAMPLE 11

Preparation of dl-1-(2-methoxyphenyl)-4-[2-(4-methoxyphenyl)-1-phenylethyl]piperazine In dimethylformamide (40 ml) are dissolved 2-(4-methoxyphenyl)-1-phenylethylamine (2.3 g) and N,N-bis(2-bromoethyl)-o-anisidine hydrobromide (4.2 g), and thereto is added sodium hydrogen carbonate (2.7 g). The mixture is heated under reflux for 10 hours under stirring. After cooling, the inorganic materials are filtered off and the filtrate is distilled to remove the solvent. To the residue is added concentrated aqueous ammonia and the mixture is extracted with ether. The ether layer is dried over anhydrous sodium sulfate and then the solvent is distilled off. The resulting residue is treated with methanolic hydrochloric acid, and the resulting crystals are recrystallized from methanol to give the desired compound as dihydrochloride monohydrate (2.7 g), m.p. 233° – 236°C.

EXAMPLE 12

Preparation of dl-1-(2-methoxyphenyl)-4-[1-phenyl-2-(4-tolyl)ethyl]piperazine

In dimethylformamide (40 ml) are dissolved 1-phenyl-2-(4-tolyl)ethylamine (2.1 g) and N,N-bis(2-chloroethyl)-o-anisidine hydrochloride (2.8 g), and thereto is added sodium hydrogen carbonate (2.7 g). The mixture is heated under reflux for 10 hours under stirring. The reaction mixture is treated in the similar manner as described in Example 11 to give the desired compound as dihydrochloride hemihydrate (2.6 g), m.p. 234° – 238°C.

EXAMPLE 13

Preparation of dl-1-cyclohexyl-4-[2-(4-methoxyphenyl)-1-phenylethyl]piperazine

To a Grignard reagent prepared from magnesium turnings (2.3 g), magnesium powder (2.3 g) and p-methoxybenzyl chloride (6.3 g) in absolute ether (83 ml) is added dropwise a solution of α-(4-cyclohexylpiperazin-1-yl)phenylacetonitrile (2.8 g) in absolute ether (10 ml) under stirring. The mixture is heated under reflux for 1.5 hours. The reaction mixture is poured onto ice water by decantation and then acidified with hydrochloric acid. The aqueous layer is separated and made alkaline with aqueous ammonia. The mixture is extracted with ether, and the ether layer is washed with water, dried over anhydrous sodium sulfate and then distilled to remove the solvent. The residue is treated with ethanolic hydrochloric acid, and the resulting crystals are recrystallized from methanol to give the desired compound as dihydrochloride (3.0 g), colorless needles, m.p. 243° – 245°C (decomp).

Example 14

Preparation of dl-1-cyclohexyl-4-[2-(4-hydroxyphenyl)-1-phenylethyl]piperazine (1) A mixture of dl-1-cyclohexyl-4-[2-(4-methoxyphenyl)-1-phenylethyl]piperazine dihydrochloride (50 g), 48 % hydrobromic acid (500 ml) and glacial acetic acid (250 ml) is heated under reflux for 4 hours and then allowed to cool. The precipitated crystals are collected by filtration, washed with a small amount of ethanol and then recrystallized from methanol to give the desired compound as dihydrobromide (52 g), colorless needles, m.p. 267° – 268.5°C.

2. A mixture of dl-1-cyclohexyl-4-[2-(4-ethoxyphenyl)-1-phenylethyl]piperazine dihydrochloride (1.5 g) and anhydrous aluminum chloride (4.0 g) is mashed well with dehumidification. The mixture is heated at 110° – 125°C for about 15 minutes under stirring under nitrogen gas. After cooling, to the reaction mixture is added ice, and the hardly soluble materials are collected by filtration and washed with a small amount of cooled diluted hydrochloric acid and further washed with acetone and ether. The materials are dissolved in water, and the mixture is made alkaline with potassium carbonate and extracted with chloroform. The chloroform layer is washed with water, dried over anhydrous sodium sulfate and then distilled to remove the solvent. The residue is treated with ethanolic hydrochloric acid and the resulting crystals are recrystallized from methanol to give the desired compound as dihydrochloride (0.8 g), m.p. 263° – 265°C.

3. In ethanol-acetic acid (1 : 1, 50 ml) is dissolved dl-1-cyclohexyl-4-[2-(4-benzyloxyphenyl)-1-phenylethyl]piperazine dihydrochloride monohydrate (0.55 g), and thereto is added 10 % palladium-charcoal (0.5 g). The mixture is subjected to catalytic reduction. When about one molar equivalent of hydrogen is absorbed, the reaction is stopped, and the catalyst is filtered off. The filtrate is distilled under a reduced pressure to remove the solvent. The resulting crystals are recrystallized from methanol to give the desired compound as dihydrochloride (0.35 g), m.p. 263° – 265°C.

The starting materials used in the above Examples are prepared as follows:

A. Preparation of N,N-bis(2-chloroethyl)-2-(4-methoxyphenyl)-1-phenylethylamine

1. To a Grignard reagent prepared from magnesium turnings (6.7 g), magnesium powder (6.7 g) and p-methoxybenzyl chloride (18.1 g) in absolute ether (240 ml) is added dropwise a solution of 3-(2-hydroxyethyl)-2-phenyloxazolidine (9.6 g) in absolute ether (24 ml) under stirring, and the mixture is heated under reflux for 3 hours. The reaction mixture is poured onto ice water (100 ml) containing ammonium chloride under vigorously stirring by decantation, and the mixture is made alkaline with ammonia. The ether layer is separated and extracted with an excess amount of 10 % hydrochloric acid. The hydrochloric acid layer is made alkaline with sodium hydroxide and extracted with chloroform. The chloroform layer is dried over anhydrous sodium sulfate and then the solvent is distilled off to give an oily substance of crude N,N-bis(2-hydroxyethyl)-2-(4-methoxyphenyl)-1-phenylethylamine (10.2 g).

2. In chloroform (16 ml) is dissolved N,N-bis(2-hydroxyethyl)-2-(4-methoxyphenyl)-1-phenylethylamine (12.6 g), and thereto is added one or two drops of dimethylformamide and further added dropwise a solution (18 ml) of thionyl chloride (12 ml) in chloroform. The mixture is heated under reflux for 3 hours and then distilled under reduced pressure to remove the solvent and the excess thionyl chloride. The resulting residue is recrystallized from acetone to give the desired compound as hydrochloride (13.4 g), m.p. 121° – 124°C.

B. Preparation of α-(4-cyclohexylpiperazin-1-yl)-phenylacetonitrile

To concentrated hydrochloric acid (5.9 g) are added N-cyclohexylpiperazine (5.1 g) and then benzaldehyde (3.2 g) under cooling, and to the mixture is added dropwise a solution of potassium cyanide (2.2 g) in water (4 ml) under stirring. The mixture is heated at 90°C for one hour under stirring, by which the mixture is solidified. The reaction mixture is dissolved in ethyl acetate and thereto is added aqueous sodium hydroxide solution to make it alkaline. After the mixture is shaken, the organic layer is separated, washed with water, dried over anhydrous sodium sulfate and then distilled under a reduced pressure to remove the solvent. The residual crystals are washed with petroleum ether, dried and recrystallized from n-hexane to give the desired compound (7.5 g), colorless needles, m.p. 79° – 81°C.

C. Preparation of dl-1-cyclohexyl-4-[2-(4-benzyloxyphenyl)-1-phenylethyl]piperazine In dimethylformamide (30 ml) are dissolved 2-(4-benzyloxyphenyl)-1-phenylethylamine (9.1 g) and N-cyclohexyl-2,2'-dichlorodiethylamine hydrochloride (2.6 g), and the mixture is heated under reflux for 6 hours under stirring. The solvent is distilled off under a reduced pressure. To the residue is added 10 % hydrochloric acid and the resulting solution is allowed to cool. The resulting crystals are collected by filtration, washed with a small amount of cooled water and then acetone, dried and recrystallized from ethanol-ether to give the desired compound as dihydrochloride monohydrate (3.1 g), m.p. 236° – 243°C (decomp).

In the same manner as described above, the following compound is prepared.

dl-1-Cyclohexyl-4-[2-(4-ethoxyphenyl)-1-phenylethyl]-piperazine, free base: m.p. 80° – 81°C, dihydrochloride: m.p. 246° – 249°C (decomp).

| Example 15 | |
|---|---|
| dl-1-Cyclohexyl-4-[2-(4-methoxyphenyl)-1-phenylethyl]piperazine dihydrochloride | 50 g |
| Starch | 110 g |
| Calcium carboxymethyl cellulose | 30 g |
| Hydroxypropyl cellulose | 9 g |
| Magnesium stearate | 1 g |

The above components are blended, granulated and made into tablets in accordance with the conventional method. The 1000 tablets each weighing 200 mg are formed.

| Example 16 | |
|---|---|
| dl-1-Cyclohexyl-4-[2-(4-methoxyphenyl)-1-phenylethyl]piperazine dihydrochloride | 25 g |
| Starch | 20 g |
| Lactose | 50 g |
| Talc | 5 g |

The above components are blended and granulated and filled into 1,000 capsules in accordance with the conventional method.

What is claimed is:

1. A compound of the formula:

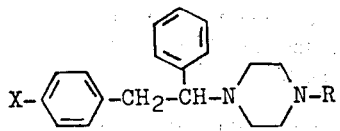

wherein X is hydroxy, methoxy, methyl or trifluoromethyl; and R is an unsubstituted monocycloalkyl group having 6 to 8 carbon atoms or 2-methoxyphenyl; provided that when X is hydroxy, R is cyclohexyl, and when X is trifluoromethyl, R is 2-methoxyphenyl, or a pharmaceutically acceptable acid addition salt thereof.

2. The compound according to claim 1, which is in dl-form.

3. 1-Cyclohexyl-4-[2-(4-methoxyphenyl)-1-phenylethyl]piperazine or a pharmaceutically acceptable acid addition salt thereof.

4. The compound according to claim 3, which is in dl-form.

5. 1-Cycloheptyl-4-[2-(4-methoxyphenyl)-1-phenylethyl]piperazine or a pharmaceutically acceptable acid addition salt thereof.

6. The compound according to claim 5, which is in dl-form.

7. 1-(2-Methoxyphenyl)-4-[1-phenyl-2-(4-tolyl)ethyl]-piperazine or a pharmaceutically acceptable acid addition salt thereof.

8. The compound according to claim 7, which is in dl-form.

9. 1-Cyclohexyl-4-[2-(4-hydroxyphenyl)-1-phenylethyl]piperazine or a pharmaceutically acceptable acid addition salt thereof.

10. The compound according to claim 9, which is in dl-form.

11. 1-Cyclohexyl-4-[1-phenyl-2-(4-tolyl)ethyl]-piperazine or a pharmaceutically acceptable acid addition salt thereof.

12. The compound according to claim 11, which is in dl-form.

13. 1-(2-Methoxyphenyl)-4-[2-(4-methoxyphenyl)-1-phenylethyl]piperazine or a pharmaceutically acceptable acid addition salt thereof.

14. The compound according to claim 13, which is in dl-form.

15. 1-Cyclooctyl-4-[2-(4-methoxyphenyl)-1-phenylethyl]piperazine or a pharmaceutically acceptable acid addition salt thereof.

16. The compound according to claim 15, which is in dl-form.

17. 1-Cycloheptyl-4-[1-phenyl-2-(4-tolyl)ethyl]-piperazine or a pharmaceutically acceptable acid addition salt thereof.

18. The compound according to claim 17, which is in dl-form.

19. 1-(2-Methoxyphenyl)-4-[1-phenyl-2-(4-trifluoromethylphenyl)ethyl]piperazine or a pharmaceutically acceptable acid addition salt thereof.

20. The compound according to claim 19, which is in dl-form.

21. 1-Cyclooctyl-4-[1-phenyl-2-(4-tolyl)ethyl]-piperazine or a pharmaceutically acceptable acid addition salt thereof.

22. The compound according to claim 21, which is in dl-form.

23. An analgesic composition consisting essentially of a compound of claim 2 as the active ingredient.

* * * * *